US007004981B2

(12) United States Patent
Yagioka et al.

(10) Patent No.: US 7,004,981 B2
(45) Date of Patent: Feb. 28, 2006

(54) METHOD OF HAIR DYEING AND HAIRDYE SET

(75) Inventors: Satoshi Yagioka, Tokyo (JP); Shoji Machida, Sayama (JP); Hiroyasu Daigo, Sayama (JP)

(73) Assignee: Arimino Co., Ltd., Tokyo (JP)

( * ) Notice: Subject to any disclaimer, the term of this patent is extended or adjusted under 35 U.S.C. 154(b) by 115 days.

(21) Appl. No.: 10/475,921

(22) PCT Filed: Sep. 26, 2002

(86) PCT No.: PCT/JP02/09951

§ 371 (c)(1),
(2), (4) Date: Oct. 27, 2003

(87) PCT Pub. No.: WO03/072074

PCT Pub. Date: Sep. 4, 2003

(65) Prior Publication Data

US 2004/0133991 A1    Jul. 15, 2004

(30) Foreign Application Priority Data

Feb. 27, 2002    (JP)    ............................... 2002-051598

(51) Int. Cl.
*A61K 7/13*    (2006.01)
(52) U.S. Cl. ...................... 8/411; 8/406; 8/408; 8/410; 8/412
(58) Field of Classification Search ................... 8/405, 8/406
See application file for complete search history.

(56) References Cited

U.S. PATENT DOCUMENTS 5,053,051 A * 10/1991 Tennigkeit et al. ............ 8/406

5,316,551 A * 5/1994 Wenke ........................... 8/406

FOREIGN PATENT DOCUMENTS

| JP | (1998) 10-167937 B2 | 6/1998 |
| JP | 2002-114644 B2 | 4/2002 |
| JP | 2002-114653 B2 | 4/2002 |
| JP | 2002-167311 B2 | 6/2002 |
| JP | 2002-241248 B2 | 8/2002 |

OTHER PUBLICATIONS

English translation for JPO website of JP 2002-241248, Aug. 28, 2002.*
Patent Abstracts of Japan, JP Publication No. 2002-097121, published Apr. 2, 2002, inventors: Toshihiko, Yamamoto et al., entitled "Oxidative Hair Dyeing Composition".

* cited by examiner

*Primary Examiner*—Margaret Einsmann
(74) *Attorney, Agent, or Firm*—The Webb Law Firm

(57) ABSTRACT

A hair-coloring method comprises coloring hair having virgin hair portions and already-colored hair portions, wherein:
(A) the virgin hair portions are colored with an oxidative hair-coloring agent (I) comprising an oxidative dye, ammonia and hydrogen peroxide and having an ammonia concentration of 0.2 to 3.0% by weight and a hydrogen peroxide concentration of 2.5 to 5.0% by weight, and
(B) the already-colored hair portions are colored with an oxidative hair-coloring agent (II) comprising an oxidative dye, ammonia and hydrogen peroxide and having an ammonia concentration of 0.1 to 1.5% by weight and a hydrogen peroxide concentration of 0.01 to 2.0% by weight.

Hair having virgin hair portions and already-colored hair portions can be colored in a uniform color tone over the whole hair.

10 Claims, No Drawings

METHOD OF HAIR DYEING AND HAIRDYE SET

TECHNICAL FIELD

The present invention relates to a hair-coloring method. More particularly, the invention relates to a method of uniformly coloring hair having virgin hair portions and already-colored hair portions and a hair-coloring agent set favorably used for the hair-coloring method.

BACKGROUND ART

Recently, the number of people who continuously have their hair colored has increased. Under such circumstances, coloring to obtain uniform color over the entire hair or coloring to change the hair to a different color is frequently requested, particularly as the hair grows.

When coloring for obtaining uniform color or coloring for changing the hair to different color is performed, coexistence of original hair having been not colored (referred to as "virgin hair" hereinafter) and hair having been already colored (referred to as "already-colored hair" hereinafter) has to be taken into consideration.

For example, in case of hair having been colored with a general oxidative hair-coloring agent, melanin has been destroyed and the dye has been gradually washed away to discolor the hair in the already-colored hair portions, and these portions have higher lightness as compared with the virgin hair portions. Therefore, even if the same hair-coloring agent is used, the already-colored hair portions exhibit color tone of higher lightness as compared with the virgin hair portions, resulting in a problem that uniform coloring over the whole hair is impossible.

Under such circumstances as mentioned above, the present inventors have earnestly studied, and as a result, they have found that uniform color tone can be realized over the whole hair by the use of different hair-coloring agents, namely, oxidative hair-coloring agents each of which contains ammonia and hydrogen peroxide in specific concentrations, for the virgin hair portions and the already-colored hair portions. Based on the finding, the present invention has been accomplished.

Accordingly, it is an object of the present invention to provide a hair-coloring method by which hair having virgin hair portions and already-colored hair portions can be colored in uniform color tone over the whole hair, and a hair-coloring agent set which is favorably used for the hair-coloring method.

SUMMARY OF THE INVENTION

The hair-coloring method according to the present invention is a hair-coloring method comprising coloring hair having virgin hair portions and already-colored hair portions, wherein:

(A) the virgin hair portions are colored with an oxidative hair-coloring agent (I) comprising an oxidative dye, ammonia and hydrogen peroxide and having an ammonia concentration of 0.2 to 3.0% by weight and a hydrogen peroxide concentration of 2.5 to 5.0% by weight, and (B) the already-colored hair portions are colored with an oxidative hair-coloring agent. (II) comprising an oxidative dye, ammonia and hydrogen peroxide and having an ammonia concentration of 0.1 to 1.5% by weight and a hydrogen peroxide concentration of 0.01 to 2.0% by weight.

In the hair-coloring method of the invention, the oxidative hair-coloring agent (I) and the oxidative hair-coloring agent (II) need to satisfy at least one of the following conditions, preferably both of them, when white yak hair is colored with these hair-coloring agents for 20 minutes at room temperature;

(i) the difference of lightness (Munsell lightness) in the Munsell color system between the hair colored with the oxidative hair-coloring agent (I) and the hair colored with the oxidative hair-coloring agent (II) is in the range of 0.2 to 3.0, and (ii) the difference of chroma (Munsell chroma) in the Munsell color system between the hair colored with the oxidative hair-coloring agent (I) and the hair colored with the oxidative hair-coloring agent (II) is in the range of 0.05 to 5.0.

The hair-coloring agent set according to the present invention comprises:

(A) a hair-coloring agent for virgin hair portions (an oxidative hair-coloring agent (I)), comprising an oxidative dye., ammonia and hydrogen peroxide and having an ammonia concentration of 0.2 to 3.0% by weight and a hydrogen peroxide concentration of 2.5 to 5.0% by weight, and (B) a hair-coloring agent for already-colored hair portions (an oxidative hair-coloring agent (II)), comprising an oxidative dye, ammonia and hydrogen peroxide and having an ammonia concentration of 0.1 to 1.5% by weight and a hydrogen peroxide concentration of 0.01 to 2.0% by weight.

In the hair-coloring agent set of the invention, the hair-coloring agent for virgin hair portions and the hair-coloring agent for already-colored hair portions need to satisfy at least one of the following conditions, preferably both of them, when white yak hair is colored with these hair-coloring agents for 20 minutes at room temperature;

(i) the difference of lightness (Munsell lightness) in the Munsell color system between the hair colored with the hair-coloring agent for virgin hair portions and the hair colored with the hair-coloring agent for already-colored hair portions is in the range of 0.2 to 3.0, and (ii) the difference of chroma (Munsell chroma) in the Munsell color system between the hair colored with the hair-coloring agent for virgin hair portions and the hair colored with the hair-coloring agent for already-colored hair portions is in the range of 0.05 to 5.0.

According to the present invention, when the virgin hair portions obtained by coloring with the oxidative hair-coloring agent (I) and the already-colored hair portions obtained by coloring with the oxidative hair-coloring agent (II) are compared, these portions have almost the same hue, lightness and chroma.

DETAILED DESCRIPTION OF THE INVENTION

The hair-coloring method according to the invention and the hair-coloring agent set preferably used for the hair-coloring method are described in detail hereinafter.

The hair-coloring method according to the invention is a hair-coloring method comprising coloring hair having virgin hair portions and already-colored hair portions, wherein:

(A) an oxidative hair-coloring agent (I) containing an oxidative dye and further containing ammonia and hydrogen peroxide in specific concentrations is applied to the virgin hair portions to color it, and (B) an oxidative hair-coloring agent (II) containing an oxidative dye and further containing ammonia and hydrogen peroxide in specific concentrations is applied to the already-colored hair portions to color it, whereby the whole hair is colored in uniform color tone.

The hair-coloring agent set according to the invention comprises:

(A) a hair-coloring agent for virgin hair portions (an oxidative hair-coloring agent (I)), containing an oxidative dye and further containing ammonia and hydrogen peroxide in specific concentrations, and (B) a hair-coloring agent for already-colored hair portions (an oxidative hair-coloring agent (II)), containing an oxidative dye and further containing ammonia and hydrogen peroxide in specific concentrations.

Hair-Coloring Agent Set

Oxidative Hair-Coloring Agent (I) and Oxidative Hair-Coloring Agent (II)

First, the oxidative hair-coloring agent (I) and the oxidative hair-coloring agent (II) for use in the invention are described.

The oxidative hair-coloring agent (I) used for the virgin hair portions of hair, i.e., hair-coloring agent for virgin hair portions, comprises an oxidative dye, ammonia and hydrogen peroxide. In the oxidative hair-coloring agent (I), the ammonia concentration is in the range of 0.2 to 3.0% by weight, preferably 0.4 to 2.0% by weight, more preferably 0.5 to 1.7% by weight, and the hydrogen peroxide concentration is in the range of 2.5 to 5.0% by weight, preferably 2.8 to 4.5% by weight, more preferably 3.0 to 4.0% by weight.

The oxidative hair-coloring agent (II) used for the already-colored hair portions of hair, i.e., hair-coloring agent for already-colored hair portions, comprises an oxidative dye, ammonia and hydrogen peroxide. In the oxidative hair-coloring agent (II), the ammonia concentration is in the range of 0.1 to 1.5% by weight, preferably 0.25 to 1.0% by weight, more preferably 0.4 to 0.7% by weight, and the hydrogen peroxide concentration is in the range of 0.01 to 2.0% by weight, preferably 0.5 to 1.8% by weight, more preferably 1.0 to 1.6% by weight.

For preparing the oxidative hair-coloring agents containing ammonia and hydrogen peroxide in the above concentrations, ammonia and hydrogen peroxide are preferably used in the form of ammonia water and hydrogen peroxide water, respectively, from the viewpoint of easy handling.

By incorporating ammonia and hydrogen peroxide in the oxidative hair-coloring agents (I) and (II), i.e., hair coloring agent for virgin hair portions and hair-coloring agent for already-colored hair portions in the above concentrations, the color tone of the virgin hair portions and that of the already colored-hair portions after coloring can be made uniform. In the vicinity of boundaries between the virgin hair portions and the already-colored hair portions, there has been conventionally observed a phenomenon that different hair-coloring agents are mixed to form a zone of different color tone. By the use of the hair-coloring agent set of the invention, however, such boundary portions can be also colored in the same uniform color tone as that of other portions, and consequently, the whole hair can be colored in uniform color tone.

That is to say, because the oxidative hair-coloring agent (I) that is the hair-coloring agent for virgin hair portions is used for the virgin hair portions, it needs to bleach hair to increase lightness of the hair, while because the oxidative hair-coloring agent (II) that is the hair-coloring agent for already-colored hair portions is used for the already-colored hair portions, it maintains the existing condition without further increasing lightness of hair, whereby both of the lightness of the virgin hair portions and the lightness of the already-colored hair portions can be controlled, and besides the chroma and the hue of both portions can be controlled to almost the same level by the action of the oxidative dye, etc.

Manufactured goods of the oxidative hair-coloring agents (I) and (II) preferably consist of a first agent containing, as main ingredients, an oxidative dye, ammonia, etc. and a second agent containing, as main ingredients, hydrogen peroxide, etc., and in the use of a hair-coloring agent set of such two-pack type, both of the agents (first agent and second agent) have only to be mixed. There is no specific limitation on the form of the first agent and the second agent, and for example, they are preferably used in the form of a liquid or a cream.

Next, the two-pack type is described.

First Agent

The first agent in each of the oxidative hair-coloring agents (I) and (II) contains an oxidative dye, ammonia and pure water as main ingredients.

The oxidative dye is not specifically restricted, and oxidative dyes publicly known are employable. The oxidative dye generally consists of a dye precursor and if necessary a coupler.

Examples of the dye precursors include p-phenylenediamine, p-aminophenol, p-methylaminophenol, p-toluenediamine (toluene-2,5-diamine), o-phenylenediamine, o-aminophenol, toluene-3,4-diamine, N,N-bis(hydroxyethyl)-p-phenylenediamine, 2-(hydroxyethyl)-p-phenylenediamine, N-phenyl-p-phenylenediamine, 4,4'-diaminodiphenylamine, 2-chloro-p-phenylenediamine, N,N-dimethyl-p-phenylenediamine, 2,6-dichloro-p-phenylenediamine, p-aminophenylsulfamic acid and 2,5-diaminopyridine.

The above dye-precursors may be used singly or in appropriate combination depending upon the color tone intended to be obtained by coloring of hair.

Examples of the couplers include meta-components, such as m-phenylenediamine and m-aminophenol, polyphenols, such as resorcin, pyrogallol, catechol, 1,2,4-benzenetriol and hydroquinone, p-amino-o-cresol (4-amino-o-cresol), 5-amino-o-cresol, 2,4-diaminophenol, toluene-3,4-diamine toluene-2,4-diamine, 2,6-diaminopyridine, 3,3'-iminodiphenol, 1,5-dihydroxynaphthalene, diphenylamine, phloroglucin, 2.4-diaminophenoxyethanol, gallic acid, tannic acid, ethyl gallate, methyl gallate, propyl gallate, Japanese gall, 1-methoxy-2-amino-4-(2-hydroxyethyl)aminobenzene and 5-(2-hydroxyethylamino)-2-methylphenl.

The p-aminophenol and the o-aminophenol can be used not only as a dye precursor but also as a coupler. The above couplers may be used singly or in appropriate combination depending upon the color tone intended to be obtained by coloring of hair.

Further, direct dyes, e.g., nitro dyes such as nitro-p-phenylenediamine, may be used when needed.

In the present invention, the dye is used in the first agent in an amount of about 0.01 to 3.0% by weight based on 100% by weight of the whole of the first agent.

As the dye for use in the oxidative hair-coloring agent (I) used for the virgin hair portions, namely, the hair-coloring agent for virgin hair portions, a dye, which is expected to develop color of higher lightness and higher chroma (vivid) of the same color type as compared with the dye for use in the oxidative hair-coloring agent (II), namely, the hair-coloring agent for already-colored hair portions, is preferably selected from the above dyes.

The oxidative hair-coloring agent (I) needs to increase lightness and chroma of hair because it is used for the virgin hair portions, and the dye used for the agent is required to satisfy the above conditions.

On the other hand, as the dye for use in the oxidative hair-coloring agent (II) used for the already-colored hair portions, a dye, which is expected to develop color of lower lightness and lower chroma. (dim) of the same color type as compared with the dye for use in the oxidative hair-coloring agent (I), is preferably selected from the above dyes. That is to say, the oxidative hair-coloring agent (II) needs to decrease lightness and chroma of hair because it is used for the already-colored hair portions, and the dye used for the agent is required to satisfy the above conditions.

More specifically, it is preferable to select such a dye that the oxidative hair-coloring agents (I) and (II), each of which is prepared by mixing the first agent consisting of the dye and other ingredients such as ammonia and pure water with the later-described second agent in a given mixing ratio, satisfy at least one of the following conditions (i) and (ii).

When white yak hair is colored with the oxidative hair-coloring agent (I) and the oxidative hair-coloring agent (II) for 20 minutes at room temperature, (i) the difference of lightness (Munsell lightness) in the Munsell color system between the hair colored with the oxidative hair-coloring agent (I), and the hair colored with the oxidative hair-coloring agent (II) is in the range of usually 0.2 to 3.0, preferably 0.6 to 2.2, and (ii) the difference of chroma (Munsell chroma) in the Munsell color system between the hair colored with the oxidative hair-coloring agent (I) and the hair colored with the oxidative hair-coloring agent (II) is in the range of usually 0.05 to 5.0, preferably 0.1 to 3.0.

It is more preferable that when white yak hair is colored with the oxidative hair-coloring agent (I) and the oxidative hair-coloring agent (II) for 20 minutes at room temperature, the hue (Munsell hue), in the Munsell color system, of the hair colored with the oxidative hair-coloring agent (I) and the hue (Munsell hue), in the Munsell color system, of the hair colored with the oxidative hair-coloring agent (II) are on almost the same level. The term "almost the same level" used herein means that the hues (Munsell hues) of both the hair are of the same color type, namely, warm color type or cool color type, and desirably means that they agree with each other regarding the 10 hues (R, YR, Y, GY, G, BG, B, PB, P, RP).

In the first agent, ammonia water of, for example, 28 wt % concentration can be used in an amount of 6 to 12% by weight based on 100% by weight of the whole of the first agent. In the use of ammonia water, the desired ammonia concentration has only to be obtained when the oxidative hair-coloring agent (I) or (II) is prepared by appropriately mixing the first agent with the second agent.

Examples of the pure water preferably used in the invention include ion-exchanged water and distilled water. The amount of the pure water used is not specifically restricted and has only to be such an amount that the ingredients used for the first agent can be sufficiently dissolved-or dispersed.

To the first agent, additives, such as surface active agent, stabilizer and oil ingredient, can be added when needed. These additives are not specifically restricted, and those publicly known are employable.

Second Agent

The second agent in each of the oxidative hair-coloring agents (I) and (II) contains hydrogen peroxide and pure water as main ingredients.

In the second agent, hydrogen peroxide water of, for example, 35 wt % concentration can be used in an amount of 13 to 17% by weight based on 100% by weight of the whole of the second agent. In the use of hydrogen peroxide water, the desired hydrogen peroxide concentration has only to be obtained when the oxidative hair-coloring agent (I) or (II) is prepared by appropriately mixing the first agent with the second agent.

The type, amount, etc. of the pure water employable for the second agent are the same as those previously described with respect to the first agent.

To the second agent, additives, such as surface active agent, oil ingredient, chelating agent and pH adjustor, can be added when needed. These additives are not specifically restricted, and those publicly known are employable.

The oxidative hair-coloring agent (I) is preferably prepared by mixing the first agent with the second agent immediately before coloring of hair (application to hair), and pH of the oxidative hair-coloring agent (I) thus prepared is preferably in the range of 9.5 to 10.5.

Also, the oxidative hair-coloring agent (II) is preferably prepared by mixing the first agent with the second agent immediately before coloring of hair (application to hair), and pH of the oxidative hair-coloring agent (II) thus prepared is preferably in the range of 9.3 to 10.1.

In the present invention, a set of the oxidative hair-coloring agent (I) as the hair-coloring agent for virgin hair portions and the oxidative hair-coloring agent (II) as the hair-coloring agent for already-colored hair portions is provided. By providing such a set, excellent long-term storage properties are exhibited. Further, each agent (first agent or second agent) can be replenished when needed, and this is convenient and economical. Moreover, because necessary agents are provided as a set, erroneous use does not brought about, and this is advantageous in the practical use. In addition, desired and prescribed effects are always exerted.

Hair-Coloring Method

Next, the hair-coloring method of the invention is described in detail.

According to the present invention, in the coloring of hair having virgin hair portions and already-colored hair portions, (A) the oxidative hair-coloring agent (I) obtained as above is applied to the virgin hair portions to color it, and (B) the oxidative hair-coloring agent (II) obtained as above is applied to the already-colored hair portions to color it, whereby the whole hair is colored in uniform color tone.

The virgin hair portions obtained by coloring with the oxidative hair-coloring agent (I) and the already-colored hair portions obtained by coloring with the oxidative hair-coloring agent (II) preferably have almost the same hue, lightness and chroma.

Although the hue, the lightness and the chroma may be confirmed by visual observation, it is desirable that the difference of lightness (Munsell lightness) in the Munsell color system between the virgin hair portions and the already-colored hair portions after coloring is in the range of usually 0.01 to 1.0, preferably 0.05 to 0.5; the difference of chroma (Munsell chroma) in the Munsell color system between the virgin hair portions and the already-colored hair portions after coloring is in the range of usually 0.01 to 1.0, preferably 0.05 to 0.5; and the hues (Munsell hues) of both the portions agree with each other regarding the 10 hues (R, YR, Y, GY, G, BG, B, PB, P, RP).

In general, the color tone obtained by coloring greatly depends upon degree of color development due to the oxidative dye itself and degree of bleaching of hair. Especially in case of hair of Japanese, the object of coloring is black hair containing a large amount of melanin, and therefore, the color tone actually obtained by coloring greatly varies depending upon degree of bleaching.

In the coloring of hair by the use of the oxidative hair-coloring agent, ammonia has not only a function of swelling hair to accelerate permeation of dye but also a function of accelerating decomposition of hydrogen peroxide to generate oxygen. Owing to the thus generated oxygen, the melanin in the hair is destroyed, whereby the hair is bleached and the oxidative dye develops color.

As described above, there is a close relationship between ammonia and hydrogen peroxide in the oxidative hair-coloring agent, and by virtue of their mutual action, coloring of hair is promoted.

In the present invention, the different oxidative hair-coloring agents (I) and (II) obtained by adding ammonia and hydrogen peroxide in specific amounts as described above were used in combination for the virgin hair portions and the already-colored hair portions, whereby the degree of bleaching of hair due to each oxidative hair-coloring agent and the tone of color developed by the oxidative dye are strictly controlled, and consequently, the virgin hair portions and the already-colored hair portions can be colored in uniform color tone. Moreover, the boundary portions between the virgin hair portions and the already-colored hair portions can also have the same uniform color tone as that of other portions. That is to say, according to the present invention, a problem that the oxidative hair-coloring agent applied to the virgin hair portions and the oxidative hair-coloring agent applied to the already-colored hair portions are mixed in the boundary portions between the virgin hair portions and the already-colored hair portions to form a zone of different color from that of other portions can be solved, and such boundary portions can also be colored in the same uniform color tone as that of other portions.

According to the present invention, hair having virgin hair portions and already-colored hair portions can be colored in uniform color tone over the whole hair.

According to the hair-coloring agent set of the invention, coloring of hair can be efficiently carried out.

EXAMPLE

The present invention is further described with reference to the following examples, but it should be construed that the invention is in no way limited to those examples.

Hair colored with oxidative hair-coloring agents prepared in the following examples and comparative examples was measured on the hue (Munsell hue), lightness (Munsell lightness) and chroma (Munsell chroma) in the Munsell color system in accordance with the methods described below.

Measuring Method Using Color-Difference Meter

About 1.5 g of a bundle of commercially available white yak hair was prepared, and to the bundle of hair, oxidative hair-coloring agents (I)-1 to (I)-7, (II)-1 to (II)-7, C1 and C2 obtained in the following examples and comparative examples were each applied in an appropriate amount, followed by allowing the bundle of hair to stand for 20 minutes at room temperature, to color the hair. The bundle of the colored yak hair was cleaned with shampoo and a rinsing liquid and then dried in a conventional manner.

Thereafter, the bundle of the colored yak hair was measured on the aforesaid items using a color-difference meter CR-200 type (manufactured by Minolta Co., Ltd., measuring light: standard light $D_{65}$, color temperature: 6504K) and setting the color system mode to MUNSELL mode.

More specifically, the bundle of the colored hair was placed on a black board, and a light receptor of the color-difference meter was pushed against the bundle of the hair to measure hue, lightness and chroma in the Munsell color system. Then, this measurement was carried out twice with changing the measuring position of the bundle of the hair, and an average value of the measurements of three times was calculated.

The results are set forth in Table 4.

Example 1

Preparation of First Agent

In accordance with the compounding proportions shown in Table 1, a first agent for virgin hair portions and a first agent for already-colored hair portions were prepared in the following manner.

First, cetanol, liquid paraffin, polyoxyethylene stearyl ether, stearyltrimethylammonium chloride and polyethylene glycol were placed in a reactor vessel equipped with a stirring device and heated at 75° C. to give a solution. With stirring the solution; a solution obtained by dissolving paraphenylenediamine, paraaminophenol, paraaminoortho-cresol and sodium sulfite in pure water at 75° C. was gradually added, then they were cooled to 30° C. with stirring, and 28 wt % ammonia water was added, to obtain creamy first agents.

Preparation of Second Agent

In accordance with the compounding proportions shown in Table 2 and using 35 wt % hydrogen peroxide water, a creamy second agent having a hydrogen peroxide content of 6% by weight and a creamy second agent having a hydrogen peroxide content of 3% by weight were prepared in a conventional manner.

Coloring and Evaluation

Hair, which had been subjected to coloring of brown type about two months before and in which the virgin hair portions were normal black hair of Japanese and the already-colored hair portions had considerably high lightness, was subjected to coloring.

First, to the virgin hair portions, an oxidative hair-coloring agent (I)-1 obtained by mixing the first agent for virgin hair portions with the second agent for virgin hair portions (hydrogen peroxide content: 6% by weight) in a mixing ratio of 1:2 (by weight) was applied. The oxidative hair-coloring agent (I)-1 had an ammonia concentration of 1.0% by weight, a hydrogen peroxide concentration of 3.8% by weight and pH of 10.3.

Immediately after the application to the virgin hair portions, to the already-colored hair portions, an oxidative hair-coloring agent (II)-1 obtained by mixing the first agent for already-colored hair portions with the second agent for already-colored hair portions (hydrogen peroxide content: 3% by weight) in a mixing ratio of 1:1 (by weight) was applied, followed by allowing the hair to stand for 15 minutes at room temperature. The oxidative hair-coloring agent (II)-1 had an ammonia concentration of 0.6% by weight, a hydrogen peroxide concentration of 1.6% by weight and pH of 9.6.

Thereafter, the hair was sufficiently cleaned with shampoo and then rinsed in a conventional manner.

As a result of evaluation of the colored hair by visual observation, the virgin hair portions and the already-colored hair portions were uniformly colored, and even in the boundary portions, the same uniform color tone as in other portions could be attained.

The results are set forth in Table 5.

Example 2

Preparation of First Agent

A first agent for virgin hair portions and a first agent for already-colored hair portions were prepared in the same manner as in Example 1, except that the compounding proportions-were changed as shown in Table 1.

Preparation of Second Agent

In accordance with the compounding proportions shown in Table 2 and using 35 wt % hydrogen peroxide water, a creamy second agent having a hydrogen peroxide content of 6% by weight and a creamy second agent having a hydrogen peroxide content of 3% by weight were prepared in a conventional manner.

Coloring and Evaluation

Hair, which had been subjected to coloring of brown type about two months before and in which the virgin hair portions were normal black hair of Japanese, the black virgin hair portions had a length of about 2 cm and the already-colored hair portions had considerably high lightness, was subjected to coloring so as to give color tone of natural type.

First, to the virgin hair portions, an oxidative hair-coloring agent (I)-2 obtained by mixing the first agent for virgin hair portions with the second agent for virgin hair portions (hydrogen peroxide content: 6% by weight) in a mixing ratio of 1:2 (by weight) was applied. The oxidative hair-coloring agent-(I)-2 had an ammonia concentration of 0.84% by weight, a hydrogen peroxide concentration of 3.8% by weight and pH of 10.2.

Immediately after the application to the virgin hair portions, to the already-colored hair portions, an oxidative hair-coloring agent (II)-2 obtained by mixing the first agent for already-colored hair portions with the second agent for already-colored hair portions (hydrogen peroxide content: 3% by weight) in a mixing ratio of 1:1 (by weight) was applied, followed by allowing the hair to stand for 15 minutes at room temperature. The oxidative hair-coloring agent (II)-2 had an ammonia concentration of 0.56% by weight, a hydrogen peroxide concentration of 1.6% by weight and pH of 10.0.

Thereafter, the hair was sufficiently cleaned with shampoo and then rinsed in a conventional manner.

As a result of evaluation of the colored hair by visual observation, the virgin hair portions and the already-colored hair portions were uniformly colored in color tone of natural type, and even in the boundary portions, the same uniform color tone as in other portions could be attained.

The results are set forth in Table 5.

Example 3

Preparation of First Agent

A first agent for virgin hair portions and a first agent for already-colored hair portions were prepared in the same manner as in Example 1, except that the compounding proportions were changed as shown in Table 1.

Preparation of Second Agent

In accordance with the compounding proportions shown in Table 2 and using 35 wt % hydrogen peroxide water, a creamy second agent having a hydrogen peroxide content of 6% by weight and a creamy second agent having a hydrogen peroxide content of 3% by weight were prepared in a conventional manner.

Coloring and Evaluation

Hair, in which the virgin hair portions and the already-colored hair portions were in the same states as those of the hair in Example 2, was subjected to coloring so as to give color tone of natural type.

First, to the virgin hair portions, an oxidative hair-coloring agent (I)-3 obtained by mixing the first agent for virgin hair portions with the second agent for virgin hair portions (hydrogen peroxide content: 6% by weight) in a mixing ratio of 1:1 (by weight) was applied. The oxidative hair-coloring agent (I)-3 had an ammonia: concentration of 1.26% by weight, a hydrogen peroxide concentration of 2.90% by weight and pH of 10.2.

After 5 minutes from the application to the virgin hair portions, to the already-colored hair portions, an oxidative hair-coloring agent (II)-3 obtained by mixing the first agent for already-colored hair portions with the second agent for already-colored hair portions (hydrogen peroxide content: 3% by weight) in a mixing ratio of 1:1 (by weight) was applied, followed by allowing the hair to stand for 15 minutes at room temperature. The oxidative hair-coloring agent (II)-3 had an ammonia concentration of 0.56% by weight, a hydrogen peroxide concentration of 1.6% by weight and pH of 10.0.

Thereafter, the: hair was sufficiently cleaned with shampoo and then rinsed in a conventional manner.

As a result of evaluation of the colored hair by visual observation, the virgin hair portions and the already-colored hair portions were uniformly colored in color tone of natural type, and even in the boundary portions, the same uniform color tone as in other portions could be attained.

The results are set forth in Table 5.

Example 4

Preparation of First Agent

A first-agent for virgin hair portions and a first agent for already-colored hair portions were prepared in the same manner as in Example 1, except that the compounding proportions were changed as shown in Table 1.

Preparation of Second Agent

In accordance with the compounding proportions shown in Table 2 and using 35 wt % hydrogen peroxide water, a creamy second agent having a hydrogen peroxide content of 6% by weight and a creamy second agent having a hydrogen peroxide content of 3% by weight were prepared in a conventional manner.

Coloring and Evaluation

Hair, in which the virgin hair portions and the already-colored hair portions were in the same states as those of the hair in Example 2, was subjected to coloring so as to give color tone of natural type.

First, to the virgin hair portions, an oxidative hair-coloring agent (I)-4 obtained by mixing the first agent for virgin hair portions with the second agent for virgin hair portions (hydrogen peroxide content: 6% by weight) in a mixing ratio of 1:1 (by weight) was applied. The oxidative hair-coloring agent (I)-4 had an ammonia concentration of 0.84% by weight, a hydrogen peroxide concentration of 2.8% by weight and pH of 10.1.

Immediately after the application to the virgin hair portions, to the already-colored hair portions, an oxidative hair-coloring agent (II)-4 obtained by mixing the first agent for already-colored hair portions wit the second agent for already-colored hair portions (hydrogen peroxide content: 3% by weight) in a mixing ratio of 1:1 (by weight) was applied, followed by allowing the hair to stand for 15 minutes at room temperature. The oxidative hair-coloring agent (II)-4 had an ammonia concentration of 0.1% by weight, a hydrogen peroxide concentration of 1.6% by weight and pH of 9.6.

Thereafter, the hair was sufficiently cleaned with shampoo and then rinsed in a conventional manner.

As a result of evaluation of the colored hair by visual observation, the boundary portions between the virgin hair portions and the already-colored hair portions became a light zone. The virgin hair portions did not seem to have hue of natural type and were slightly darker as compared with the already-colored hair portions. The already-colored hair portions were slightly lighter as compared with the virgin hair portions and had poor uniformity of finished color.

The results are set forth in Table 5.

Example 5

Preparation of First Agent

A first agent for virgin hair portions and a first agent for already-colored hair portions were prepared in the same manner as in Example 1, except that the compounding proportions were changed as shown in Table 1.

Preparation of Second Agent

In accordance with the compounding proportions shown in Table 2 and using 35 wt % hydrogen peroxide water, a creamy second agent having a hydrogen peroxide content of 6% by weight and a creamy second agent having a hydrogen peroxide content of 3% by weight were prepared in a conventional manner.

Coloring and Evaluation

Hair, in which the virgin hair portions and the already-colored hair portions were in the same states as those of the hair in Example 2, was subjected to coloring so as to give color tone of red type.

First, to the virgin hair portions, an oxidative hair-coloring agent (I)-5 obtained by mixing the first agent for virgin hair portions with the second agent for virgin hair portions (hydrogen peroxide content: 6% by weight) in a mixing ratio of 1:2 (by weight) was applied. The oxidative hair-coloring agent (I)-5 had an ammonia concentration of 0.84% by weight, a hydrogen peroxide concentration of 3.8% by weight and pH of 10.4.

Immediately after the application to the virgin hair portions, to the already-colored hair portions, an oxidative hair-coloring agent (II)-5 obtained by mixing the first agent for already-colored hair portions with the second agent for already-colored hair portions (hydrogen peroxide content: 3% by weight) in a mixing ratio of 1:1 (by weight) was applied, followed by allowing the hair to stand for 15 minutes at room temperature. The oxidative hair-coloring agent (II)-5 had an ammonia concentration of 0.56% by weight, a hydrogen peroxide concentration of 1.6% by weight and pH of 9.9.

Thereafter, the hair was sufficiently cleaned with shampoo and then rinsed in a conventional manner.

As a result of evaluation of the colored hair by visual observation, the virgin hair portions and the already-colored hair portions were uniformly colored in color tone of red type, and even in the boundary portions, the same uniform color tone as in other portions could be attained.

The results are set forth in Table 5.

Example 6

Preparation of First Agent

A first agent for virgin hair portions and a first agent for already-colored hair portions were prepared in the same manner as in Example 1, except that the compounding proportions were changed as shown in Table 1.

Preparation of Second Agent

In accordance with the compounding proportions shown in Table 2 and using 35 wt % hydrogen peroxide water, a creamy second agent having a hydrogen peroxide content of 6% by weight and a creamy second agent having a hydrogen peroxide content of 3% by weight were prepared in a conventional manner.

Coloring and Evaluation

Hair, in which the virgin hair portions and the already-colored hair portions were in the same states as those of the hair in Example 2, was subjected to coloring so as to give color tone of red type.

First, to the virgin hair portions, an oxidative hair-coloring agent (I)-6 obtained by mixing the first agent for virgin hair portions with the second agent for virgin hair portions (hydrogen peroxide content: 6% by weight) in a mixing ratio of 1:1 (by weight) was applied. The oxidative hair-coloring agent (I)-6 had an ammonia concentration of 1.26% by weight, a hydrogen peroxide concentration of 2.90% by weight and pH of 10.1.

After 5 minutes from the application to the virgin hair portions, to the already-colored hair portions, an oxidative hair-coloring agent (II)-6 obtained by mixing the first agent for already-colored hair portions with the second agent for already-colored hair portions (hydrogen peroxide content: 3% by weight) in a mixing ratio of 1:1 (by weight) was applied, followed by allowing the hair to stand for 15 minutes at room temperature. The oxidative hair-coloring agent (II)-6 had an ammonia concentration of 0.56% by weight, a hydrogen peroxide concentration of 1.7% by weight and pH of 9.9.

Thereafter, the hair was sufficiently cleaned with shampoo and then rinsed in a conventional manner.

As a result of evaluation of the colored hair by visual observation, the virgin hair portions and the already-colored hair portions were uniformly colored in color tone of red type, and even in the boundary portions, the same uniform color tone as in other portions could be attained.

The results are set forth in Table 5.

Example 7

Preparation of First Agent

A first agent for virgin hair portions and a first agent for already-colored hair portions were prepared in the same manner as in Example 1, except that the compounding proportions were changed as shown in Table 3.

Preparation of Second Agent

In accordance with the compounding proportions shown in Table 2 and using 35 wt % hydrogen peroxide water, a creamy second agent having a hydrogen peroxide content of 6% by weight and a creamy second agent having a hydrogen peroxide content of 3% by weight were prepared in a conventional manner.

Coloring and Evaluation

Hair, in which the virgin hair portions and the already-colored hair portions were in the same states as those of the hair in Example 2, was subjected to coloring so as to give color tone of red type.

First, to the virgin hair portions, an oxidative hair-coloring agent (I)-7 obtained by mixing the first agent for virgin hair portions with the second agent for virgin hair portions (hydrogen peroxide content: 6% by weight) in a mixing ratio of 1:1 (by weight) was applied. The oxidative hair-coloring agent (I)-7 had an ammonia concentration of 0.84% by weight, a hydrogen peroxide concentration of 2.8% by weight and pH of 10.3.

Immediately after the application to the virgin hair portions, to the already-colored hair portions, an oxidative hair-coloring agent (II)-7 obtained by mixing the first agent for already-colored hair portions with the second agent for already-colored hair portions (hydrogen peroxide content: 3% by weight) in a mixing ratio of 1:1 (by weight) was applied, followed by allowing the hair to stand for 1.5 minutes at room temperature. The oxidative hair-coloring agent (II)-7 had an ammonia concentration of 0.1% by weight, a hydrogen peroxide concentration of 1.6% by weight and pH of 9.6.

As a result of evaluation of the colored hair by visual observation, the boundary portions between the virgin hair portions and the already-colored hair portions became a light zone. The virgin hair portions did not seem to have hue of red type and were slightly darker as compared with the already-colored hair portions. The already-colored hair portions were slightly lighter as compared with the virgin hair portions and had poor uniformity of finished color.

The results are set forth in Table 5.

Comparative Examples 1 and 2

Preparation of First Agent

First agents were prepared in the same manner as in Example 1, except that the compounding proportions were changed as shown in Table 3.

Preparation of Second Agent

In accordance with the compounding proportions shown in Table 2, a creamy second agent having a hydrogen peroxide content of 6% by weight and a creamy second agent having a hydrogen peroxide content of 3% by weight were prepared in a conventional manner.

Coloring and Evaluation

Hair, in which the virgin hair portions and the already-colored hair portions were in the same states as those of the hair in Example 1, was subjected to coloring in the following manner.

(1) An oxidative hair-coloring agent C1 obtained by mixing the first agent for Comparative Example 1 with the second agent for Comparative Example 1 (hydrogen peroxide content: 3% by weight) in a mixing ratio of 1:1 (by weight) was applied to the virgin hair portions and the already-colored hair portions, followed by allowing the hair to stand for 20 minutes at room temperature. The subsequent operations were carried out in the same manner as in Example 1. The oxidative hair-coloring agent C1 had an ammonia concentration of 0.1% by weight, a hydrogen peroxide concentration of 1.6% by weight and pH of 8.0.

As a result of evaluation of the colored hair by visual observation, the boundary portions between the virgin hair portions and the already-colored hair portions became a dark zone. The virgin hair portions had extremely lower lightness as compared with the already-colored hair portions and did not have uniform finished color.

The results are set forth in Table 5.

(2) An oxidative hair-coloring agent C2 obtained by mixing the first agent for Comparative Example 2 with the second agent for Comparative Example 2 (hydrogen peroxide content: 6% by weight) in a mixing ratio of 1:1 (by weight) was applied to the virgin hair portions and the already-colored hair portions, followed by allowing the hair to stand for 20 minutes at room temperature. The subsequent operations were carried out in the same manner as in Example 1. The oxidative hair-coloring agent. C2 had an ammonia concentration of 1.0% by weight, a hydrogen peroxide concentration of 2.8% by weight and pH of. 10.0.

As a result of evaluation of the colored hair by visual observation, the boundary portions between the virgin hair portions and the already-colored hair portions became a light zone. The virgin hair portions had extremely higher lightness than the desired lightness and did not have uniform finished color.

The results are set forth in Table 5.

TABLE 1

| | First agent | | | | | | | |
|---|---|---|---|---|---|---|---|---|
| | Ex. 1 | | EX. 2 and Ex. 3 | | Ex. 4 | | Ex. 5 and Ex. 6 | |
| | Virgin hair portion | Already-colored hair portion | Virgin hair portion | Already-colored hair portion | Virgin hair portion | Already-colored hair portion | Virgin hair portion | Already-colored hair portion |
| p-Phenylene-diamine | 0.02 | 0.2 | 0.15 | 0.58 | 0.08 | 0.17 | 0.25 | 0.57 |
| Resorcin | — | — | 0.15 | 0.18 | 0.05 | 0.20 | — | 0.25 |
| m-Amino-phenol | — | — | — | 0.05 | — | — | — | 0.09 |
| p-Amino-ortho-cresol | 0.5 | 0.25 | 0.015 | 0.05 | — | 0.02 | 0.32 | 0.54 |
| p-Amino-phenol | 0.5 | 0.9 | — | 0.24 | — | — | 0.25 | 0.36 |

TABLE 1-continued

| | First agent | | | | | | | |
|---|---|---|---|---|---|---|---|---|
| | Ex. 1 | | EX. 2 and Ex. 3 | | Ex. 4 | | Ex. 5 and Ex. 6 | |
| | Virgin hair portion | Already-colored hair portion | Virgin hair portion | Already-colored hair portion | Virgin hair portion | Already-colored hair portion | Virgin hair portion | Already-colored hair portion |
| Nitro-paraphenyl-enediamine | — | — | — | — | — | — | 0.15 | 0.05 |
| Cetanol | 4.0 | 4.0 | 4.0 | 4.0 | 4.0 | 4.0 | 4.0 | 4.0 |
| Liquid paraffin | 8.0 | 8.0 | 8.0 | 8.0 | 8.0 | 8.0 | 8.0 | 8.0 |
| Polyoxyethylene stearyl ether | 5.0 | 5.0 | 5.0 | 5.0 | 5.0 | 5.0 | 5.0 | 5.0 |
| Stearyl-trimethyl-ammonium chloride | 1.0 | 1.0 | 1.0 | 1.0 | 1.0 | 1.0 | 1.0 | 1.0 |
| Polyethylene glycol | 5.0 | 5.0 | 5.0 | 5.0 | 5.0 | 5.0 | 5.0 | 5.0 |
| Sodium sulfite | 0.3 | 0.3 | 0.6 | 0.6 | 0.6 | 0.6 | 0.6 | 0.6 |
| 28% Ammonia water | 11.0 | 4.0 | 9.0 | 4.0 | 6.0 | 1.0 | 9.0 | 4.0 |
| Pure water | | | | to make up to 100 | | | | |

Notes:
The unit for each value in the table is "% by weight".

TABLE 2

| | Second agent | |
|---|---|---|
| | Hydrogen peroxide content: 6 wt % | Hydrogen peroxide content: 3 wt % |
| Cetanol | 2.0 | 2.0 |
| Liquid paraffin | 4.0 | 4.0 |
| Polyoxyethylene stearyl ether | 5.0 | 5.0 |
| Stearyltrimethylammonium chloride | 1.0 | 1.0 |
| Polyethylene glycol | 5.0 | 5.0 |
| 35 wt % Hydrogen peroxide water | 16.0 | 9.0 |
| 85 wt % phosphoric acid | 0.1 | 0.1 |
| Phenacetin | 0.1 | 0.1 |
| Pure water | to make up to 100 | |

TABLE 3

| | First agent | | | |
|---|---|---|---|---|
| | Ex. 7 | | | |
| | Virgin hair portion | Already-colored hair portion | Comp. Ex. 1 | Comp. Ex. 2 |
| p-Phenylenediamine | 0.05 | 0.25 | 0.1 | 0.2 |
| Resorcin | 0.05 | — | — | — |
| m-Aminophenol | 0.15 | — | — | — |
| p-Aminoorthocresol | — | 0.6 | 0.35 | 0.1 |
| p-Aminophenol | — | 0.2 | 0.7 | 0.5 |
| Nitro-paraphenylenediamine | 0.15 | — | — | — |
| Cetanol | 4.0 | 4.0 | 4.0 | 4.0 |
| Liquid paraffin | 8.0 | 8.0 | 8.0 | 8.0 |
| Polyoxyethylene stearyl ether | 5.0 | 5.0 | 5.0 | 5.0 |
| Stearyltrimethylammonium chloride | 1.0 | 1.0 | 1.0 | 1.0 |
| Polyethylene glycol | 5.0 | 5.0 | 5.0 | 5.0 |
| Sodium sulfite | 0.6 | 0.6 | 0.3 | 0.3 |
| 28% Ammonia water | 6.0 | 1.0 | 1.0 | 7.0 |
| Pure water | to make up to 100 | | | |

Notes:
The unit for each value in the table is "% by weight".

TABLE 4

| | Oxidative hair-coloring agent | Hue (H) | Lightness (V) | Chroma (C) |
|---|---|---|---|---|
| Ex. 1 | (I)-1 | 1.5 YR | 4.1 | 6.9 |
| | (II)-1 | 2.2 YR | 3.3 | 3.9 |
| Ex. 2 | (I)-2 | 1.2 YR | 3.6 | 1.4 |
| | (II)-2 | 9.8 R | 1.9 | 1.2 |
| Ex. 3 | (I)-3 | 1.8 YR | 4.0 | 1.3 |
| | (II)-3 | 9.8 R | 1.9 | 1.2 |
| Ex. 4 | (I)-4 | 7.8 YR | 5.3 | 1.6 |
| | (II)-4 | 1.2 YR | 3.7 | 2.2 |
| Ex. 5 | (I)-5 | 7.2 R | 2.5 | 4.5 |
| | (II)-5 | 4.6 R | 1.9 | 2.5 |
| Ex. 6 | (I)-6 | 7.6 R | 2.9 | 4.7 |
| | (II)-6 | 4.6 R | 1.9 | 2.5 |
| Ex. 7 | (I)-7 | 8.2 YR | 3.9 | 5.1 |
| | (II)-7 | 4.4 R | 3.2 | 4.7 |
| Comp. Ex. 1 | C1 | 1.2 YR | 3.6 | 4.4 |
| Comp. Ex. 2 | C2 | 4.1 YR | 4.6 | 2.6 |

TABLE 5

|  | Ex. 1 | Ex. 2 | Ex. 3 | Ex. 4 | Ex. 5 | Ex. 6 | Ex. 7 | Comp. Ex. 1 | Comp. Ex. 2 |
|---|---|---|---|---|---|---|---|---|---|
| Results | AA | AA | AA | A | AA | AA | A | B | B |

Evaluation:
AA: The uniformity in the virgin hair portions and the already-colored hair portions after coloring is excellent, and the boundary portions between the virgin hair portions and the already-colored hair portions have the same uniform color tone as that of other portions.
A: The uniformity after coloring is slightly poor, and the boundary portions between the virgin hair portions and the already-colored hair portions are lighter as compared with other portions.
B: The uniformity after coloring is lacking, and the boundary portions between the virgin hair portions and the already-colored hair portions are extremely lighter as compared with other portions.

As described above, the hair-coloring method of the invention is useful for uniformly coloring hair having virgin hair portions and already-colored hair portions. The hair-coloring agent set of the invention is favorably used in the hair-coloring method of the invention and is suitable for use by barbers and beauty parlor professionals.

What is claimed is:

1. A hair-coloring method comprising coloring hair having virgin hair portions and already-colored hair portions, wherein:
   (A) the virgin hair portions are colored with an oxidative hair-coloring agent (I) comprising an oxidative dye, ammonia, hydrogen peroxide and pure water and having an ammonia concentration of 0.2 to 3.0% by weight and a hydrogen peroxide concentration of 2.5 to 5.0% by weight and being prepared by mixing a first agent containing the oxidative dye in an amount of 0.01 to 3.0% by weight, the ammonia and pure water with a second agent containing the hydrogen peroxide and pure water, and
   (B) the already-colored hair portions are colored with an oxidative hair-coloring agent (II) comprising an oxidative dye, ammonia, hydrogen peroxide and pure water and having an ammonia concentration of 0.1 to 1.5% by weight and a hydrogen peroxide concentration of 0.01 to 2.0% by weight and being prepared by mixing a first agent containing the oxidative dye in an amount of 0.01 to 3.0% by weight, the ammonia and pure water with a second agent containing the hydrogen peroxide and pure water.

2. The hair-coloring method as claimed in claim 1, wherein when the virgin hair portions obtained by coloring with the oxidative hair-coloring agent (I) and the already-colored hair portions obtained by coloring with the oxidative hair-coloring agent (II) are compared, these portions have almost the same hue, lightness and chroma.

3. A hair-coloring agent set comprising:
   (A) a hair-coloring agent for virgin hair portions (an oxidative hair-coloring agent (I)), comprising an oxidative dye, ammonia, hydrogen peroxide and pure water and having an ammonia concentration of 0.2 to 3.0% by weight and a hydrogen peroxide concentration of 2.5 to 5.0% by weight and being prepared by mixing a first agent containing the oxidative dye in an amount of 0.01 to 3.0% by weight, the ammonia and pure water with a second agent containing the hydrogen peroxide and pure water, and
   (B) a hair-coloring agent for already-colored hair portions (an oxidative hair-coloring agent (II)), comprising an oxidative dye, ammonia, hydrogen peroxide and pure water and having an ammonia concentration of 0.1 to 1.5% by weight and a hydrogen peroxide concentration of 0.01 to 2.0% by weight and being prepared by mixing a first agent containing the oxidative dye in an amount of 0.01 to 3.0% by weight, the ammonia and pure water with a second agent containing the hydrogen peroxide and pure water.

4. The hair-coloring agent set as claimed in claim 3, wherein when virgin hair portions obtained by coloring with the hair-coloring agent for virgin hair portions and already-colored hair portions obtained by coloring with the hair-coloring agent for already-colored hair portions are compared, these portions have almost the same hue, lightness and chroma.

5. The hair-coloring method as claimed in claim 1, wherein the oxidative dye of the oxidative hair-coloring agent (I) is obtained from
   at least one dye precursor selected from the group consisting of p-phenylenediamine, p-aminophenol, p-methylaminophenol, p-toluenediamine, o-phenylenediamine and o-aminophenol, or
   at least one coupler selected from the group consisting of m-phenylenediamine, m-aminophenol, resorcin and p-amino-o-cresol and at least one said dye precursor.

6. The hair-coloring method as claimed in claim 1, wherein the oxidative dye of the oxidative hair-coloring agent (II) is obtained from
   at least one dye precursor selected from the group consisting of p-phenylenediamine, p-aminophenol, p-methylaminophenol, p-toluenediamine, o-phenylenediamine and o-aminophenol, or
   at least one coupler selected from the group consisting of m-phenylenediamine, m-aminophenol, resorcin and p-amino-o-cresol and at least one said dye precursor.

7. The hair-coloring method as claimed in claim 1, wherein the oxidative dye of the oxidative hair-coloring agent (I) is selected so as to develop color of higher lightness and of the same color type as compared with the oxidative dye of the oxidative hair-coloring agent (II) and
   the oxidative dye of the oxidative hair-coloring agent (II) is selected so as to develop color of lower lightness and of the same color type as compared with the oxidative dye of the oxidative hair-coloring agent (I).

8. The hair-coloring agent as claimed in claim 3, wherein the oxidative dye of the oxidative hair-coloring agent (I) is obtained from
   at least one dye precursor selected from the group consisting of p-phenylenediamine, p-aminophenol, p-methylaminophenol, p-toluenediamine, o-phenylenediamine and o-aminophenol, or
   at least one coupler selected from the group consisting of m-phenylenediamine, m-aminophenol, resorcin and p-amino-o-cresol and at least one said dye precursor.

9. The hair-coloring agent set as claimed in claim 3, wherein the oxidative dye of the oxidative hair-coloring agent (II) is obtained from
   at least one dye precursor selected from the group consisting of p-phenylenediamine, p-aminophenol, p-methylaminophenol, p-toluenediamine, o-phenylenediamine and o-aminophenol, or
   at least one coupler selected from the group consisting of m-phenylenediamine, m-aminophenol, resorcin and p-amino-o-cresol and at least one said dye precursor.

10. The hair-coloring agent set as claimed in claim 3, wherein the oxidative dye of the oxidative hair-coloring agent (I) is selected so as to develop color of higher lightness and of the same color type as compared with the oxidative dye of the oxidative hair-coloring agent (II) and
    the oxidative dye of the oxidative hair-coloring agent (II) is selected so as to develop color of lower lightness and of the same color type as compared with the oxidative dye of the oxidative hair-coloring agent (I).

* * * * *

UNITED STATES PATENT AND TRADEMARK OFFICE
CERTIFICATE OF CORRECTION

PATENT NO. : 7,004,981 B2 Page 1 of 1
APPLICATION NO. : 10/475921
DATED : February 28, 2006
INVENTOR(S) : Yagioka et al.

It is certified that error appears in the above-identified patent and that said Letters Patent is hereby corrected as shown below:

<u>Face of the Patent</u>, See Item (57) ABSTRACT, Line 1, "A hair-coloring method comprises…" should read
-- A method for hair-coloring and hair-coloring agent set. The method comprising… --

<u>Face of the Patent</u>, See Item (57) ABSTRACT, Lines 15-18,
"weight.

Hair having virgin hair portions and already-colored hair portions can be colored in a uniform color tone over the whole hair." should read -- weight. The hair-coloring agent set is preferably used for the hair-coloring method, whereby, hair having virgin hair portions and already-colored hair portions can be colored in uniform color tone over the entire hair. --

Signed and Sealed this

First Day of August, 2006

JON W. DUDAS
*Director of the United States Patent and Trademark Office*